United States Patent
Hakky

(10) Patent No.: US 11,730,600 B2
(45) Date of Patent: *Aug. 22, 2023

(54) PENILE PROSTHESIS COMPRISING A RESERVOIR ATTACHABLE TO A PUMP BY CONNECTORS

(71) Applicant: Coloplast A/S, Humlebaek (DK)

(72) Inventor: Tariq Hakky, Johns Creek, GA (US)

(73) Assignee: Coloplast A/S, Humlebaek (DK)

( * ) Notice: Subject to any disclaimer, the term of this patent is extended or adjusted under 35 U.S.C. 154(b) by 351 days.

This patent is subject to a terminal disclaimer.

(21) Appl. No.: 16/985,233

(22) Filed: Aug. 5, 2020

(65) Prior Publication Data

US 2020/0360144 A1 Nov. 19, 2020

Related U.S. Application Data

(63) Continuation of application No. 15/945,746, filed on Apr. 5, 2018, now Pat. No. 10,765,520.

(60) Provisional application No. 62/481,824, filed on Apr. 5, 2017.

(30) Foreign Application Priority Data

Apr. 5, 2018 (EP) .................... 18165814

(51) Int. Cl.
*A61F 2/26* (2006.01)
*A61F 2/00* (2006.01)
*A61B 17/34* (2006.01)

(52) U.S. Cl.
CPC .......... *A61F 2/26* (2013.01); *A61F 2/004* (2013.01); *A61B 17/3468* (2013.01); *A61F 2250/0003* (2013.01); *A61F 2250/0007* (2013.01)

(58) Field of Classification Search
CPC ....... A61F 2/26; A61F 5/41; A61F 2250/0007
See application file for complete search history.

(56) References Cited

U.S. PATENT DOCUMENTS

| | | | |
|---|---|---|---|
| 7,048,682 B2 * | 5/2006 | Neisz | A61B 17/3468 600/30 |
| 10,765,520 B2 * | 9/2020 | Hakky | A61F 2/26 |
| 2006/0264700 A1 * | 11/2006 | Guy | A61H 21/00 600/38 |
| 2012/0157764 A1 * | 6/2012 | Borgaonkar | A61F 2/26 600/40 |
| 2016/0008162 A1 | 1/2016 | Daniel | |

FOREIGN PATENT DOCUMENTS

| | | | | |
|---|---|---|---|---|
| GB | 1549315 A | 7/1979 | | |
| GB | 2139090 A | 11/1984 | | |
| WO | WO-0162182 A2 * | 8/2001 | .......... | A61F 5/4404 |

* cited by examiner

*Primary Examiner* — Thaddeus B Cox
(74) *Attorney, Agent, or Firm* — Coloplast Corp., Coloplast A/S; Nick Baumann

(57) ABSTRACT

A penile prosthesis includes an inflatable cylinder implantable into a penis; a pump fluidically attachable to the inflatable cylinder through a first tube; and a reservoir attachable to the pump through a second tube that is fluidically attachable between the pump and the reservoir. Connectors are provided to couple the reservoir and the pump. A first connector includes a plurality of protrusions and a second connector includes an outer shell forming a plurality of openings. The protrusions mate with the openings to form a connection.

7 Claims, 6 Drawing Sheets

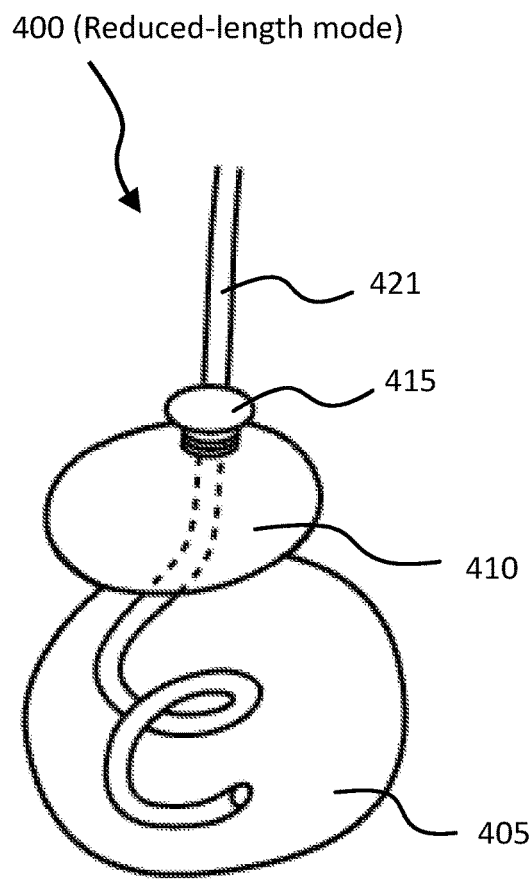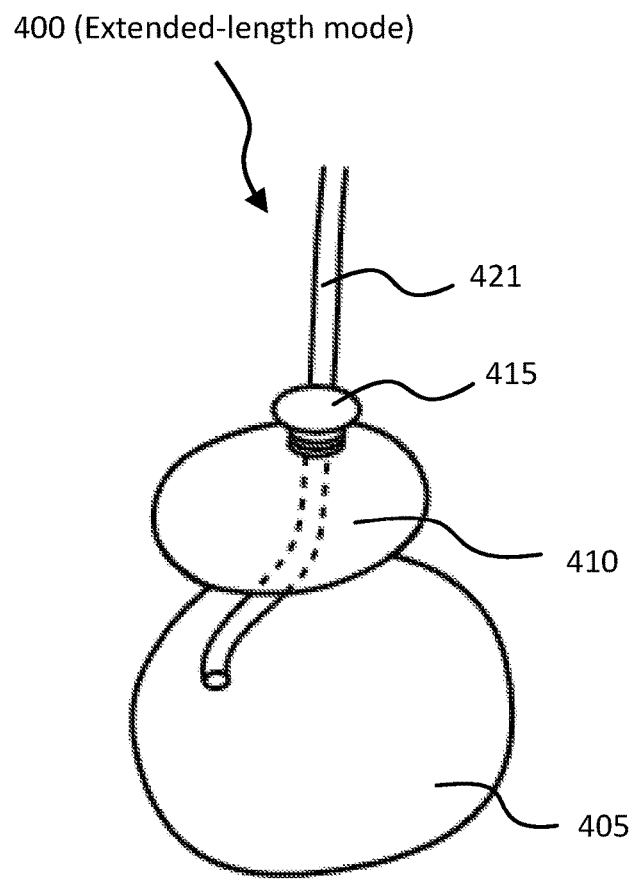
FIG. 4A
FIG. 4B

PENILE PROSTHESIS COMPRISING A RESERVOIR ATTACHABLE TO A PUMP BY CONNECTORS

FIELD OF THE INVENTION

The disclosure relates to implantable penile prosthesis. More specifically, the disclosure relates to penile implant with length-adjustable tubes.

BACKGROUND OF THE INVENTION

Penile implant is a treatment for erectile dysfunction. A particular type of penile implant device, commonly known as a three-piece device, includes a pair of inflatable cylinders that are implanted into the corpus cavernosae of the penis. The inflatable cylinders are connected to a fluid-filled reservoir through a pump and valve assembly. Such a pump and valve assembly is typically implanted into the scrotum of the patient, while the reservoir is implanted in the abdomen. Tubing is used to connect each cylinder to the pump, and additional tubing is used to connect the pump to the reservoir.

To inflate the cylinders, the patient can typically actuate the pump using one of a variety of methods that cause fluid to be transferred from the reservoir through the pump and into the cylinders. This results in the inflation of the cylinders and produces rigidity for a normal erection. When the patient desires to deflate the cylinders, the patient may manipulate a valve assembly within the pump in such a manner that the fluid in the prosthesis is released back into the reservoir. Additional manipulation of the cylindrical prosthesis may also be required. This removal of fluid from the cylinders returns the penis to a flaccid state while simultaneously refilling the reservoir with fluid.

A penile prosthesis, which is otherwise functioning, may have tubing connecting the pump and the cylinders either too long or too short. Different patients have different lengths of scrotum and need different lengths of the tubes. Currently there is no such penile implant that provides length-adjustable tubes that can be adjusted during the surgery. The embodiments disclosed herein relates to penile implant with length-adjustable tubes.

SUMMARY

The disclosure relates to implantable penile prosthesis. More specifically, the disclosure relates to penile implant with length-adjustable tubes. According to one embodiment of the disclosure, a penile prosthesis includes a pump. The penile prosthesis includes a reservoir, the reservoir being fluidically connected to the pump. The penile prosthesis includes an inflatable cylinder, the inflatable cylinder being fluidically connected to the pump through a length-adjustable tube. The length-adjustable tube includes a structural mechanism configured to adjust a length of the length-adjustable tube individually according to a patient's unique anatomy.

According to another embodiment of the disclosure, a method of implanting a penile prosthesis includes: making an incision at a base of the penis; accessing a corpus cavernosum; dilating the corpus cavernosum; inserting an inflatable cylinder into the corpus cavernosum; making an incision on a scrotum; inserting a pump into the scrotum; connecting the pump and the inflatable cylinder with a tube, wherein the tube includes length adjusting mechanisms; adjusting a length of the tube through the length adjusting mechanisms according to an anatomy. Embodiments provide a penile prosthesis, comprising a pump; a reservoir fluidically connected to the pump; at least one inflatable cylinder configured to inflate in response to actuation of the pump by a user to transfer fluid into the at least one inflatable cylinder; and at least one length-adjustable tube fluidically connecting the pump to the at least one inflatable cylinder and configured to adjust in length according to a patient's unique anatomy. One aspect of the embodiment provides the at least one length-adjustable tube includes an accordion-like structure configured to extend in length in response to an extension force longitudinally extending accordion-like structure. One aspect of the embodiment provides the accordion-like structure having two ends with one of the two ends attached to the pump and another of the two ends attached to the at least one inflatable cylinder, and the accordion-like structure is configured to extend in length by pulling the two ends away from each other. One aspect of the embodiment provides that the accordion-like is configured to reduce in length in by pushing the two ends of the accordion-like structure longitudinally toward each other. One aspect of the embodiment provides that the accordion-like structure is configured to decrease in length in response to a longitudinal contraction force contracting the accordion-like structure. One aspect of the embodiment provides that the at least one length-adjustable tube includes a nut configured to loosen and allows the at least one length-adjustable tube to be pulled from the pump to extend the length and pushed back into the pump to reduce the length. One aspect of the embodiment provides that the reservoir is fluidically connected to the pump through a second length-adjustable tube, wherein the second length-adjustable tube includes a second structural mechanism configured to adjust a length of the second length-adjustable tube according to a patient's unique anatomy. One aspect of the embodiment provides that the reservoir is fluidically connected to the pump through the second length-adjustable tube, a connector, and a flexible tube. One aspect of the embodiment provides that the connector connects the flexible tube to the length-adjustable tube. One aspect of the embodiment provides that the connector includes a male connector and a female connector, with the male connector being configured to connect with the female connector and wherein the male connector includes a plurality of protrusions disposed circumferentially about a tube and the female connector includes a plurality of openings, a tube and a circumferential recess disposed between the tube of the female connector and an outer shell of the female connector, the plurality of openings of the female connector being configured to receive the protrusions of the male connector. One aspect of the embodiment provides that the tube of the female connector is configure to insert into a lumen of the tube of the male connector. One aspect of the embodiment provides that the at least one inflatable cylinder includes a first inflatable cylinder and a second inflatable cylinder, and the at least one length-adjustable tube includes a first length-adjustable tube and a second length-adjustable tube. One aspect of the embodiment provides that the first length-adjustable tube and the second length-adjustable tube are configured to be individually adjusted according to the unique anatomy of the patient. One aspect of the embodiment provides a valve assembly arranged within the pump configured to actuate to release fluid in the at least one inflatable cylinder back into the reservoir to deflate at least one cylinder. One aspect of the embodiment provides that the at least one length-adjustable tube includes a nut configured to facilitate adjustment of the at least one length-adjustable tube and the nut is removably secured to the valve assembly. Other embodiments provide a method of implanting a penile prosthesis, comprising inserting an inflatable cylinder into the penis; inserting a pump into the scrotum; connecting the pump and the inflatable cylinder with a length-adjustable tube; and adjusting a length of the length-adjustable tube according to a patient's unique anatomy. One aspect of the embodiment provides that the length-adjustable tube includes an accordion-like structure and adjusting the length the length-adjustable tube includes at least one of longitudinally extending the accordion-like structure or longitudinally contracting the accordion-like structure. One aspect of the embodiment provides that the length-adjustable tube includes a nut configured to loosen and allow adjusting of the length of the length-adjustable tube by pulling the length-adjustable tube from the pump to extend the length and pushing the length-adjustable tube back into the pump to reduce the length. Another embodiment provides a penile prosthesis, comprising a pump; a valve assembly arranged with the pump; a reservoir fluidically connected to the pump by a first length-adjustable tube configured to adjust in length; and an inflatable cylinder fluidically connected to the pump by a second length-adjustable tube configured to adjust in length, the inflatable cylinder being configured to: inflate transfer fluid into the inflatable cylinder from the reservoir in response to actuation of the pump by a user, and deflate and release the fluid from the inflatable cylinder back into the reservoir in response to actuation of the valve assembly. One aspect of the embodiment provides that each of the first length-adjustable tube and the second-length adjustable tube are separable configured to adjust in length according to a patient's unique anatomy.

BRIEF DESCRIPTION OF THE DRAWINGS

The following drawings form part of the present specification and are included to further demonstrate certain aspects of the disclosure. The disclosure may be better understood by reference to one or more of these drawings in combination with the detailed description of the specification embodiments presented herein.

FIG. 4A is a schematic drawing of an assembly of pump and length-adjustable tubes in a reduced-length mode according to one embodiment of the disclosure.

FIG. 4B is a schematic drawing of an assembly of pump and length-adjustable tubes in an extended-length mode according to one embodiment of the disclosure.

DETAILED DESCRIPTION

Figure 1:
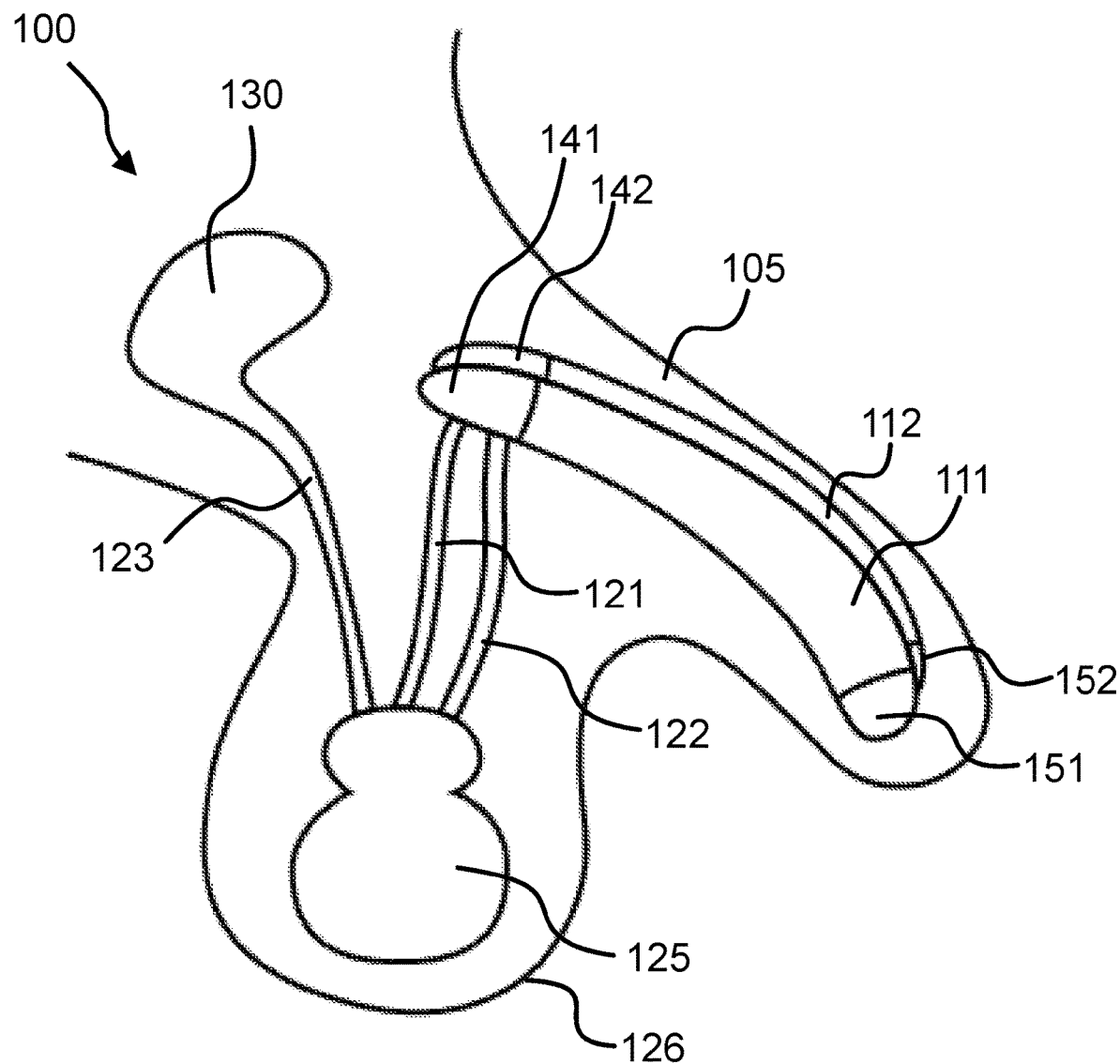
FIG. 1 is a schematic drawing of an inflatable penile prosthesis according to one embodiment of the disclosure.

The following includes definitions of various terms and phrases used throughout this specification.

The term "penile prosthesis" and the term "penile implant" may be used interchangeably in this disclosure.

The terms "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or "preventing" or "avoiding" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The methods of the present disclosure can "comprise," "consist essentially of," or "consist of" particular ingredients, components, compositions, etc. disclosed throughout the specification. With respect to the transitional phase "consisting essentially of," in one non-limiting aspect, a basic and novel characteristic of the methods is the ability to efficiently implant penile prosthesis cylinders.

Other objects, features and advantages of the present disclosure will become apparent from the following figures, detailed description, and examples. It should be understood, however, that the figures, detailed description, and examples, while indicating specific embodiments of the disclosure, are given by way of illustration only and are not meant to be limiting. Additionally, it is contemplated that changes and modifications within the spirit and scope of the disclosure will become apparent to those skilled in the art from this detailed description.

Unless defined otherwise, all technical and scientific terms used herein have the same meanings as commonly understood by one of ordinary skill in the art to which this disclosure belongs. All publications and patents specifically mentioned herein are incorporated by reference in their entirety for all purposes including describing and disclosing the chemicals, instruments, statistical analyses and methodologies which are reported in the publications which might be used in connection with the disclosure. All references cited in this specification are to be taken as indicative of the level of skill in the art. Nothing herein is to be construed as an admission that the disclosure is not entitled to antedate such disclosure by virtue of prior disclosure.

These and other non-limiting aspects of the present disclosure are discussed in further detail in the following paragraphs.

FIG. 1 is a schematic drawing of an inflatable penile prosthesis 100 according to one embodiment of the disclosure. The inflatable penile prosthesis 100 may be the inflatable penile prosthesis 200. The inflatable penile prosthesis 100 may include the pump and tubing assembly 300. The inflatable penile prosthesis 100 may include the pump and tubing assembly 400.

In FIG. 1, a penile prosthesis 100 is implanted in a penis 105. The penile prosthesis 100 includes at least two inflatable cylinders 111, 112, a pump 125, and a reservoir 130. The reservoir 130 is fluidically connected to the pump 125 through a length-adjustable tube 123. The length-adjustable tube 123 may include one or more mechanisms such that the tubing length can be individually adjusted according to the unique anatomy of the patient receiving the penile prosthesis 100. Mechanisms for length-adjustable tube 123 may include, without limitation, accordion-like structures 232, 515 (e.g., as shown in and described in further with reference to FIGS. 2 and 5), a tightening nut 615 (e.g., as shown in and described in further with reference to FIG. 6), and the like.

In addition and similar of the connection between the reservoir 130 and the pump 125, the pump 125 may also be fluidically connected to the inflatable cylinders 111, 112 through length-adjustable tubes 121, 122, respectively. The length-adjustable tubes 121, 122 may include mechanisms such that the tubing length can be individually adjusted according to the unique anatomy of the patient receiving the penile prosthesis 100. Appropriate mechanisms for length-adjustable tubes 121, 122, may include accordion-like structures 251, 252, 331, 332 (e.g., as shown in and described in further with reference to FIGS. 2 and 3), tightening nut 415 (e.g., as shown in and described in further with reference to FIG. 4), and the like.

The inflatable cylinders 111, 112 include a rear end bases 141, 142, respectively. The inflatable cylinders 111, 112 include distal tips 151, 152, respectively. In one embodiment, the distal tips 151, 152 may be made with silicon. In one embodiment, the distal tips 151, 152 may not be inflatable.

As shown in FIG. 1, the pump 125 is implanted in the scrotum 126. The reservoir 130 is stored in the patient's abdomen. In one embodiment, the reservoir 130 and the pump 125 may be integrated as one device, e.g., a pump/reservoir assembly. In one embodiment, the pump/reservoir assembly may be stored in the patient's abdomen.

In one embodiment, for a normal erection, the patient may actuate the pump 125 and fluid is transferred from the reservoir 130 through the pump 125 and into the cylinders 111, 112. When the patient desires to deflate the cylinders 111, 112, a valve assembly within the pump 125 may be actuated in a manner such that the fluid in the cylinders 111, 112 is released back into the reservoir 130.

In one embodiment, the surgical process of implantation may be invasive. To reach a corpora cavernosa of the penis 105 for implanting the cylinders 111, 112, the surgeon may make an incision at the base of the penis, such as where it meets the scrotum 126. The corpus cavernosum may be dilated to create space for the cylinder. Once corpus cavernosum is dilated, the surgeon may insert a needle guiding tool into the dilated corpus cavernosum, e.g., a Furlow. The outer surface of the needle guiding tool may be rigid yet smooth, such that the guiding tool may be smoothly pushed into the corpus cavernosum. The needle guiding tool may have an internal cavity for the needle to pass through. For example, in one embodiment, the Furlow may be a long slender device having a hollow barrel with a plunger device as an obturator at the rearward end. The plunger device may force the needle forward along the hollow barrel. The needle may be a relatively heavy, long needle, e.g., Keith needle, appropriate for piercing through body tissue.

In one embodiment, in order to guide the cylinder of the penile prosthesis to the desired position within the corpus cavernosum, the needle may be attached to a suture that is also attached to the cylinders 111, 112. The suture may attach to the cylinders 111, 112 by penetrating through one or more suture holes disposed on the distal tips 115, 152.

In one embodiment, the needle guiding tool may be first advanced into the corpus cavernosum until the forward end is inside of the crown of the penis. At this point, a deflated cylinders 111, 112 attached to a suture, which is further attached to a needle may remain outside of the patient's body. Then, the needle may be inserted into the hollow barrel of the needle guiding tool and be forced forward until out of the front end of the hollow barrel. The surgeon may grasp the needle from outside of the body and pull it from the penis leaving the suture threaded through the corpus cavernosum. The needle guiding tool may be then withdrawn from the body. The suture may then be pulled to draw the cylinder 110 into the corpus cavernosum through the incision. The suture may be pulled until the cylinder 110 is in a desired position. Then, the suture is removed.

The pump 125 is implanted into the scrotum 126 through another incision made on the scrotum 126. The tubing 121, 122 connecting the pump 125 and the cylinders 111, 112 are checked for the appropriate length. Adjusting the length of each tubing 111, 112 individually according to each patient's anatomy. Closing the incision.

In one embodiment, the length-adjustable tube 123 may be disconnected in its original state and may require to be connected during the surgery. After connecting the length-adjustable tube 123, the surgeon may adjust the length of the length-adjustable tube 123 according to the patient's anatomy.

Figure 2:
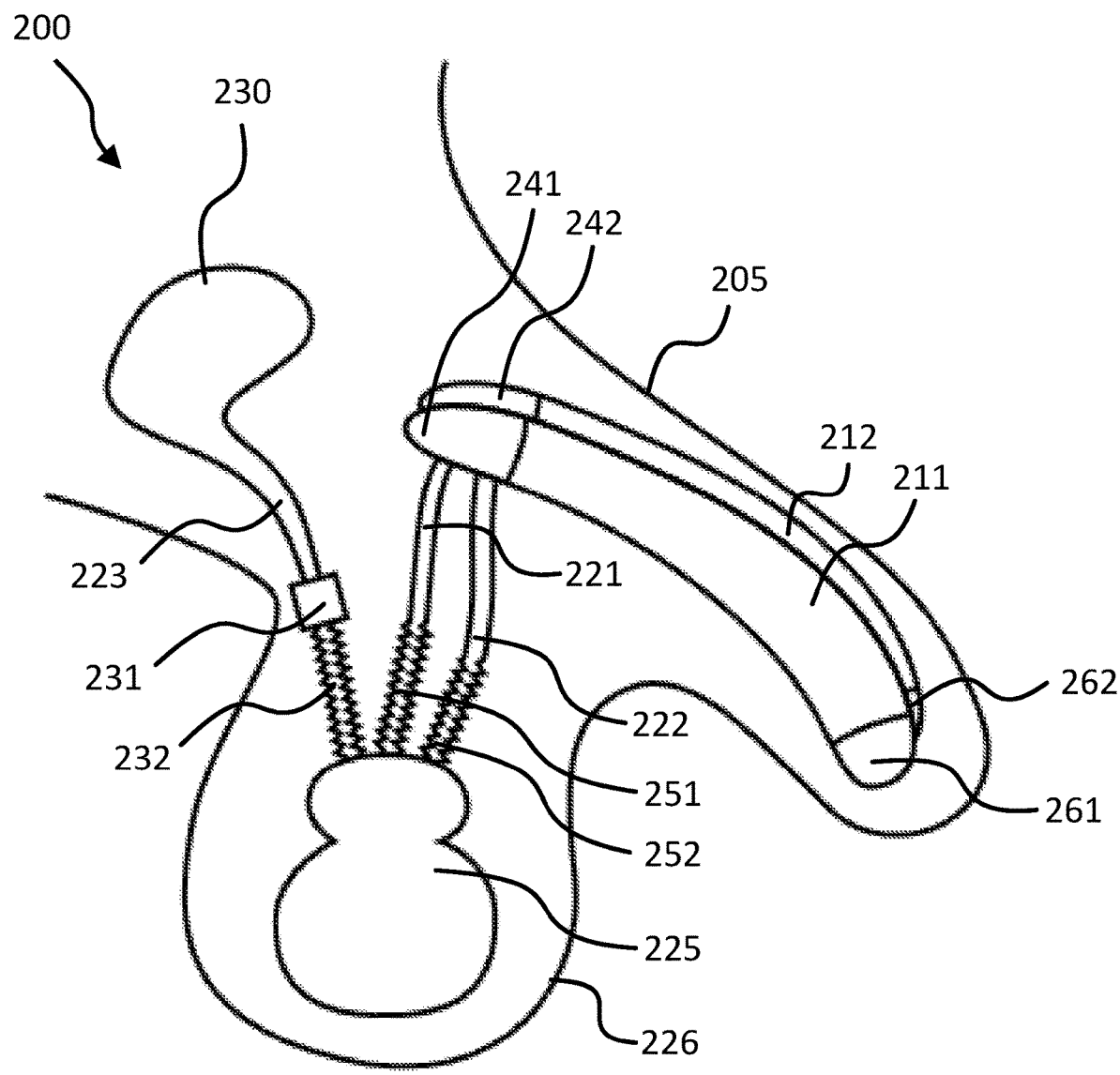
FIG. 2 is a schematic drawing of an inflatable penile prosthesis with length-adjustable tubes according to one embodiment of the disclosure.

FIG. 2 is a schematic drawing of an inflatable penile prosthesis 200 with length-adjustable tubes according to one embodiment of the disclosure. The inflatable penile prosthesis 200 may be the inflatable penile prosthesis 100. The inflatable penile prosthesis 200 may include the pump and tubing assembly 300. The inflatable penile prosthesis 100 may include the pump and tubing assembly 400.

As shown in FIG. 2, a penile prosthesis 200 is implanted in a penis 205. The penile prosthesis 200 includes at least two inflatable cylinders 211, 212, a pump 225, and a reservoir 230. The reservoir 230 is fluidically connected to the pump 225 through a length-adjustable tube 232, a connector 231, and a flexible tube 223. As shown in FIG. 2, the length-adjustable tube 232 includes an accordion-like structure 232. The accordion-like structure 232 is configured to be adjustable for adjusting the length of the tube 232. The accordion-like structure 232 is configured to be adjusted according to the unique anatomy of the patient receiving the penile prosthesis 200.

The connector 231 connects the flexible tube 223 of the reservoir 230 and the length-adjustable tube 232 of the pump 225. The connector 231 may include a male fitting and a female fitting, or any other tube fitting mechanisms currently known in the art.

The pump 225 is fluidically connected to the inflatable cylinders 211, 212 through length-adjustable tubes 221, 222, respectively. The length-adjustable tubes 221, 222 include accordion-like structures 251, 252. The accordion-like structures 251, 252 are configured to be adjustable for adjusting the length of the tubing. The accordion-like structures 251, 252 are configured to be individually adjusted according to the unique anatomy of the patient receiving the penile prosthesis 200.

In one embodiment, the accordion-like structure 251, 252, 232 can be longitudinally extended to increase the tubing length. In one embodiment, the accordion-like structure 251, 252, 232 can be pulled to extend the length. In another embodiment, the accordion-like structure 251, 252, 232 can be longitudinally contracted to decrease the tubing length. In another embodiment, the accordion-like structure 251, 252, 232 can be pushed together to reduce the tubing length.

The inflatable cylinders 211, 212 include rear end bases 241, 242, respectively. The inflatable cylinders 211, 212 include distal tips 261, 262, respectively. In one embodiment, the distal tips 261, 262 may be made with silicon. In one embodiment, the distal tips 261, 262 may not be inflatable.

As shown in FIG. 2, the pump 225 is implanted in the scrotum 226. The reservoir 230 is stored in the patient's abdomen. In one embodiment, the reservoir 230 and the pump 225 may be integrated as one device, e.g., a pump/reservoir assembly. In one embodiment, the pump/reservoir assembly may be stored in the patient's abdomen.

In one embodiment, for a normal erection, the patient may actuate the pump 225 and fluid is transferred from the reservoir 230 through the pump 225 and into the cylinders 211, 212. When the patient desires to deflate the cylinders 211, 212, a valve assembly within the pump 225 may be actuated in a manner such that the fluid in the cylinders 211, 212 is released back into the reservoir 230.

Figure 3A:
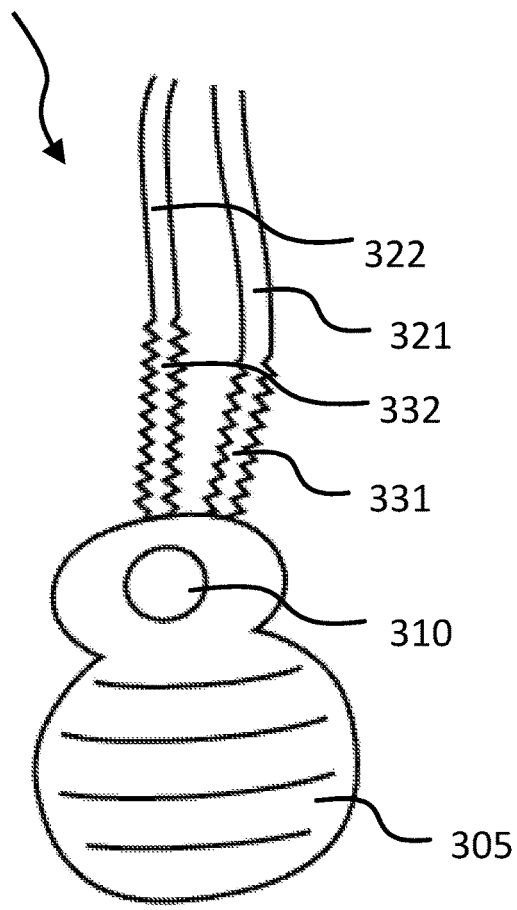
FIG. 3A is a schematic drawing of an assembly of pump and length-adjustable tubes in a reduced-length mode according to one embodiment of the disclosure.
Figure 3B:
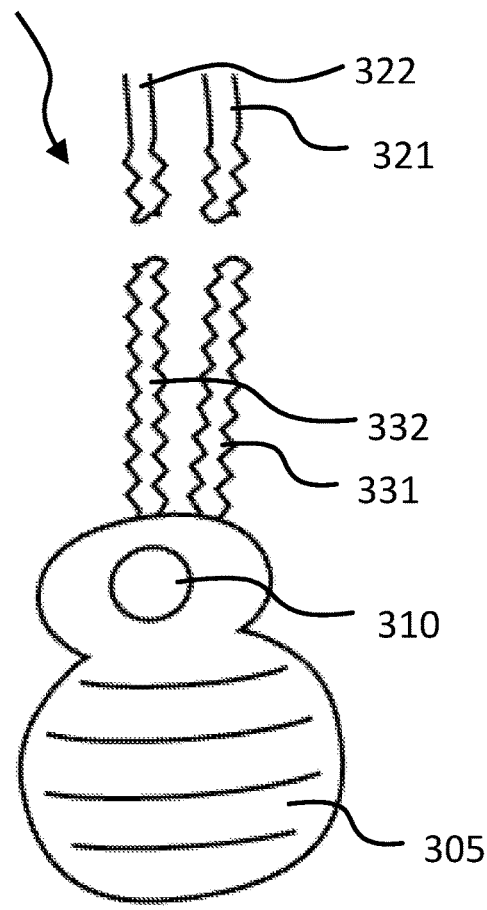
FIG. 3B is a schematic drawing of an assembly of pump and length-adjustable tubes in an extended-length mode according to one embodiment of the disclosure.

FIGS. 3A and 3B is a schematic drawing of an assembly 300 of a pump 305 and length-adjustable tubes 321, 322 according to one embodiment of the disclosure. FIG. 3A is showing the length-adjustable tubes 321, 322 in a reduced length mode according to one embodiment of the disclosure. FIG. 3B is showing the length-adjustable tubes 321, 322 in an extended-length mode according to one embodiment of the disclosure. The pump 305 includes a valve set 310 configured to allow fluid flowing from the cylinders back to a reservoir.

As shown in FIGS. 3A and 3B, the assembly 300 includes a pump 305. The pump 305 may be fluidically connected to a pair of inflatable cylinders (see FIG. 1 and FIG. 2 for example) through the length-adjustable tubes 321, 322. The tubing 321, 322 include accordion-like structures 331, 332, respectively.

As shown in FIG. 3A, both accordion-like structures 331, 332 are in a reduced-length mode. Each one of the accordion-like structures 331, 332 has two ends disposed longitudinally away from each other on a tubing. In one embodiment, the reduced-length mode can be realized by pressing the two ends longitudinally closer to each other.

As shown in FIG. 3B, both accordion-like structures 331, 332 are in an extended-length mode. In one embodiment, the extended-length mode can be realized by pulling the two ends longitudinally away from each other. As shown in comparing FIGS. 3A and 3B, folds of the accordion-like structures 331, 332 are extended in the extended-length mode.

FIGS. 4A and 4B is a schematic drawing of an assembly 400 of a pump 405 and a length-adjustable tube 421 according to one embodiment of the disclosure. FIG. 4A is a schematic drawing of an assembly 400 of a pump 405 and a length-adjustable tube 421 in a reduced-length mode according to one embodiment of the disclosure. FIG. 4B is a schematic drawing of an assembly 400 of pump 405 and length-adjustable tube 421 in an extended-length mode according to one embodiment of the disclosure.

It is noted, FIGS. 4A and 4B shows a single length-adjustable tube 421, instead of two, for the purpose of clearer graphical presentation. The assembly 400 may include two tubing, similar to FIGS. 1-2 and FIGS. 3A and 3B.

The assembly 400 includes a pump 405. The pump 405 is fluidically connected to one or more inflatable cylinders through tubing 421. The pump 405 includes a valve set 410 configured to allow fluid flowing from the cylinders back to a reservoir.

The assembly 400 includes a length-adjustable tube 421 and a nut 415. The nut 415 is removably and/or releasably secured to the valve set 410.

In one embodiment, the nut 415 has at least two positions. In a first position, the nut 415 is tightly secured to the valve set 410. When the nut is in the first position, the length-adjustable tube 421 is secured in place and cannot be pulled or pushed to make any longitudinal movement and/or length adjustment.

In another embodiment, the nut 415 can be in a second position. In the second position, the nut 415 is loosened up from the valve set. When the nut 415 is loosened up, the length-adjustable tube 421 can be pulled further out from the pump to extend the length of the tubing. At the same time, when the nut 415 is loosened up, the length-adjustable tube 421 can be pushed back into the pump to reduce the length of the tubing.

Figure 5:
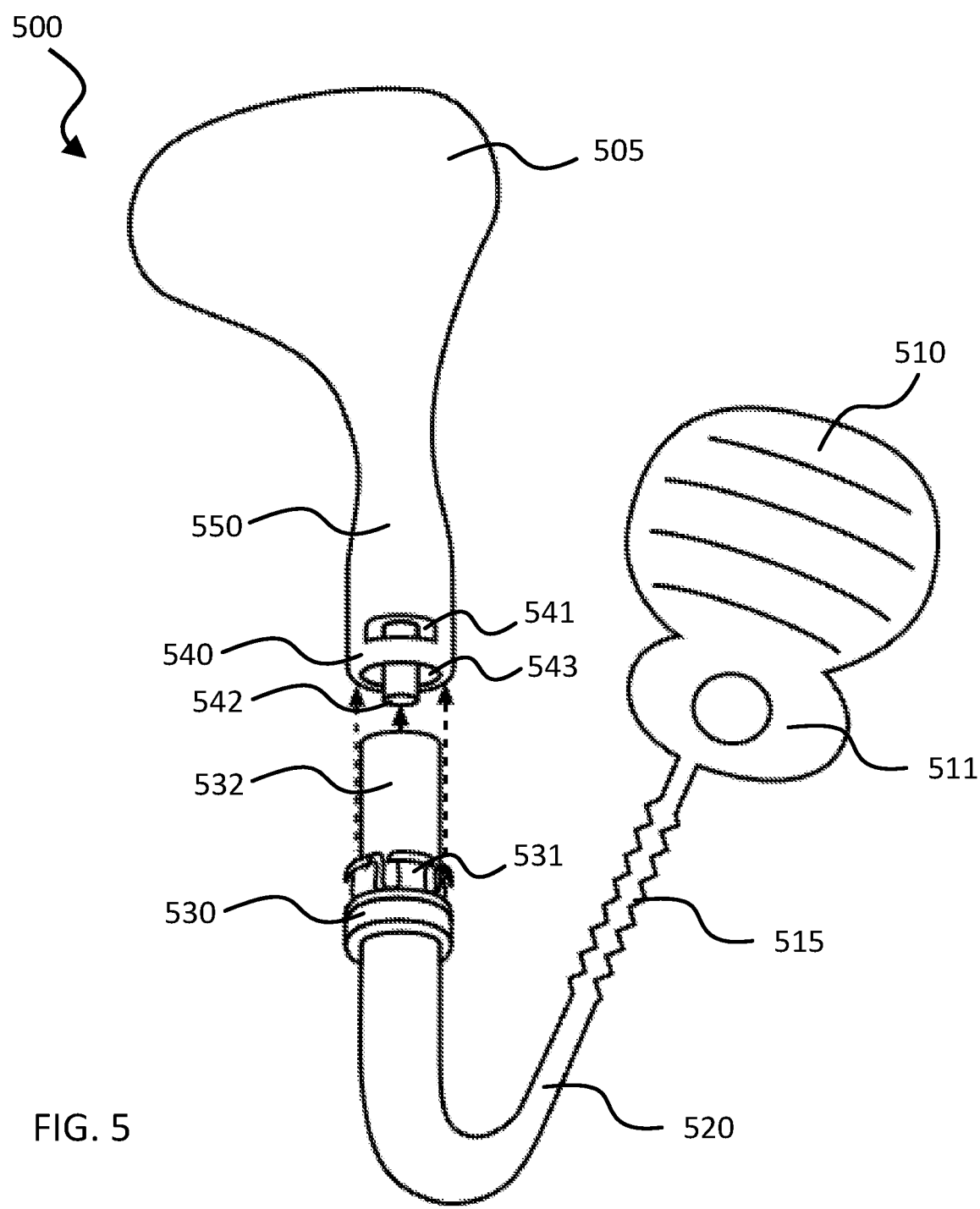
FIG. 5 is a schematic drawing of an assembly of a pump connected to a reservoir.

FIG. 5 is a schematic drawing of an assembly 500 of a pump 510 connected to a reservoir 505. The assembly 500 may be included in the penile implants 100, 200. The assembly 500 may be combined with the assemblies 300, 400.

As shown in FIG. 5, the pump 510 includes valve assembly 511. The pump 510 further includes a tube 520. The tube 520 includes an accordion-like structure 515 configured for length adjustment. The tube 520 further includes a male connector 530. The male connector 530 is configured to connect with female connector 540. The male connector 530 includes a plurality of protrusions 531 disposed circumferentially about the tube 532.

The reservoir 505 includes a tube 550. The tube 550 includes a female connector 540. The female connector 540 includes a plurality of openings 541. The openings 541 are configured to receive the protrusions 531 of the male connector 530. The female connector 540 includes a tube 542. The female connector 540 includes a circumferential recess 543 disposed between the tube 542 and the outer shell of the female connector 540.

When connecting the pump 510 and the reservoir 505, the tube 542 of the female connector 540 may be inserted into a lumen of the tube 532 of the male connector 530. The tube 532 of the male connector 530 may fit into the circumferential recess 543 of the female connector 540. The protrusions 531 of the male connector 530 may fit into the openings 541 of the female connector 540. When connecting the male connector 530 and the female connector 540, a specialized plier with one arm holding the male connector 530 and the other arm holding the female connector 540 may be used to squeeze the two connectors tightly together.

The accordion-like structure 515 has two has two ends disposed longitudinally away from each other on a tubing. In one embodiment, the reduced-length mode can be realized by pressing the two ends longitudinally closer to each other.

In one embodiment, the extended-length mode can be realized by pulling the two ends longitudinally away from each other.

Figure 6:
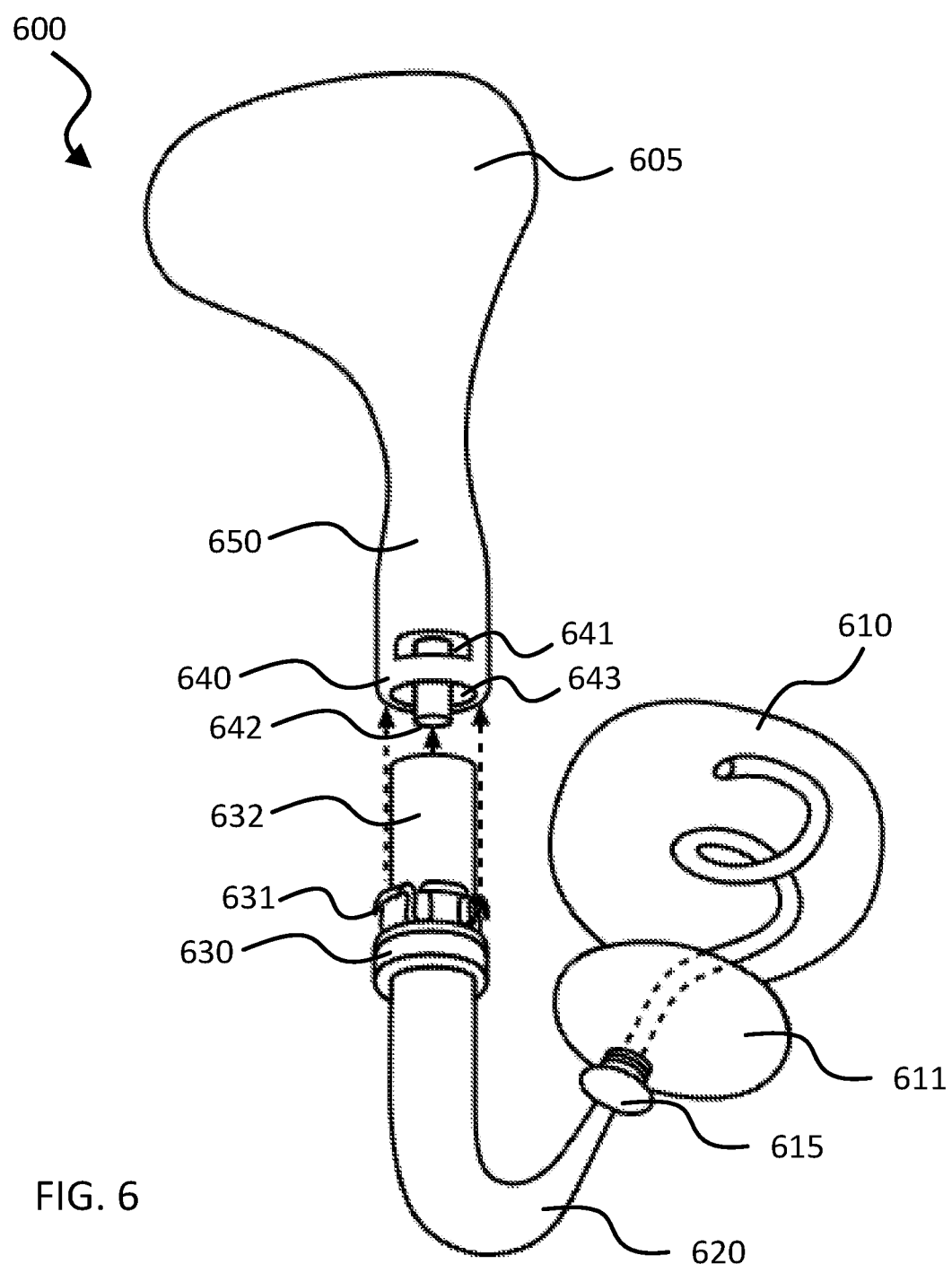
FIG. 6 is a schematic drawing of an assembly of a pump connected to a reservoir.

FIG. 6 is a schematic drawing of an assembly 600 of a pump 610 connected to a reservoir 605. The assembly 600 may be included in the penile implants 100, 200. The assembly 600 may be combined with the assemblies 300, 400.

As shown in FIG. 6, the pump 610 includes valve assembly 611. The pump 610 further includes a tube 620. The tube 620 is connected to the pump 610 through a nut 615 configured for length adjustment. The tube 620 further includes a male connector 630. The male connector 630 is configured to connect with female connector 640. The male connector 630 includes a plurality of protrusions 631 disposed circumferentially about the tube 632.

The reservoir 605 includes a tube 650. The tube 650 includes a female connector 640. The female connector 640 includes a plurality of openings 641. The openings 641 are configured to receive the protrusions 631 of the male connector 630. The female connector 640 includes a tube 642. The female connector 640 includes a circumferential recess 643 disposed between the tube 642 and the outer shell of the female connector 640.

When connecting the pump 610 and the reservoir 605, the tube 642 of the female connector 640 may be inserted into a lumen of the tube 632 of the male connector 630. The tube 632 of the male connector 630 may fit into the circumferential recess 643 of the female connector 640. The protrusions 631 of the male connector 630 may fit into the openings 641 of the female connector 640. When connecting the male connector 630 and the female connector 640, a specialized plier with one arm holding the male connector 630 and the other arm holding the female connector 640 may be used to squeeze the two connectors tightly together.

In another embodiment, a surgical method of using the various embodiments of penile prosthesis with length-adjustable tubes (e.g., 100, 200, 300, 400, 500, 600) disclosed herein includes the following steps.

Inserting a foley catheter into the urethra and the bladder is emptied. Applying a spigot. Placing a Scott retractor below a penis. Making a transverse skin incision at the penoscrotal junction. Modifying the incision an inverted T-shape and extended when better corporal exposure is needed during difficult surgery, e.g., when there is corporal fibrosis.

Exposing the dartos fascia. Placing skin hooks. Exposing the tunica albuginea of both corporas. Palpating the urethral catheter in the midline, configured to facilitate urethral exposure and minimizes its potential damage. Making a stab wound with a scalpel into each corpora.

Performing a 2-cm vertical cut between two nonabsorbable 2-0 stay sutures using Metzenbaum scissors. Performing corporal dilatation directed laterally to avoid urethral injury, wherein a dilator can be felt proximally to hit on the ischiopubic ramus, and an equal depth of the dilators should be achieved when performing proximal dilatation. This reduces the risk of proximal perforation.

Irrigating both corporas with antibiotic solution. Palpating distally the glans of the penis until maximal limit of dilatation is achieved by feeling the tip of the dilator bilaterally. Recording, at each side, a proximal and a distal measurements each towards approximately mid-point of the corporotomy incision and, adding together the proximal and distal measurements which determines the final length of the cylinder implant. Performing cycling of the connected corporal cylinders using sterile saline. Ensuring the removal of any air bubble.

Clamping gently length-adjustable tubes with rubber-shod clamps. Optionally, attaching the rear tip extenders of the cylinders. Inserting the proximal part of the corporal cylinder/rear tip extender. Inserting the Furlow instrument distally and laterally to avoid any crossover-perforation into the contralateral corporal space. Passing a Keith needle at the tip on each side to facilitate the distal placement of the cylinders through the Furlow.

Closing the corporotomies using the 2-0 absorbable stay sutures. Making a subdartos pouch for the pump in the middle of the scrotum or the hemiscrotum. Making a small incision through the dartos fascia and a long-blade nasal speculum or ring forceps is used to create the space. Inserting the pump into the subdartos pouch, ensuring that the deflation button/valve assembly lies anteriorly and inferiorly.

Passing the length-adjustable tubes from the pump through separate stab incisions in the dartos fascia to emerge from the posterior aspect of the pouch. Adjusting the length of the length-adjustable tubes.

In one embodiment, if the length-adjustable tubes includes accordion-like structures, e.g., 251, 252, 331, 332, the adjusting of the length may include pulling a two ends of the accordion-like structure longitudinally away from each other to extend the length. Or, alternatively, pushing the two ends of the accordion-like structures longitudinally toward each other to reduce the length. The length extension or reduction are done according to an anatomy of the patient.

In another embodiment, if the length-adjustable tubes includes nuts, e.g., 415, the adjusting of the length may include releasing the nut and pulling the length-adjustable tubes further out from the pump to extend the length. Or, alternatively, releasing the nut and pushing the length-adjustable tubes further back into the pump to reduce the length. The length extension or reduction are done according to an anatomy of the patient. After a desired length of the tube is adjusted, the length of the tube may be fixed in place by tightening the nut.

Closing the opening of the top part of the pouch with 2-0 nonabsorbable suture. Connecting the tubes of the pump with the cylinders.

The following steps relates to insertion of the reservoir into the abdomen. The reservoir tubing from the pump remains intact at this stage. Attaching a 50-ml syringe filled with normal saline to the reservoir tubing. This allows testing of the prosthesis cylinders to ensure the function and quality of erection. In preparation for the reservoir placement, removing the spigot from the Foley catheter and the bladder is fully drained. The selection of the size of the reservoir depends upon patient's anatomy. Identifying an external ring using a small Deaver retractor and the index finger is used to palpate the spermatic cord, pushing it medially to protect it.

A closed Metzenbaum scissors is then used to puncture the transversalis fascia. Accessing the retropubic space. Creating the space by inserting the index finger. The retropubic location of the space is confirmed by feeling the back of the pubic bone, the symphysis pubis and the Foley balloon inside the bladder. A long-blade nasal speculum is inserted through the created transversalis fascia defect, the blades are gently spread apart, and the reservoir is inserted into the newly created retropubic space. Alternatively, a Deaver can be placed to expose the space to permit placement of the reservoir. The reservoir is then filled with normal saline up to 5 mL above its manufactured capacity. With the tubing to the filling syringe left open, the syringe should spontaneously fill to 5 ml. If it fills more than this, the position of the reservoir space needs to be checked again to ensure that there is no pressure around the reservoir. Some reservoirs have lockout valves to prevent autoinflation. The correct position of the reservoir is confirmed again by palpation and it is ensured that the reservoir tubing is exiting through the transversalis fascia defect.

In one embodiment, connecting the tube 223 of the reservoir 230 and the tube 232 of the pump 225 through a connector 231. The connection may be made using an appropriate plier. After the connection is made, adjusting the length of the tube 232 to an appropriate length according to the patient's anatomy.

The final connection between the pump and the reservoir is completed and a last check is made of the connections between the three tubes. The rubber-shod clamps are removed and inflation and deflation of the prosthesis is carried out few times to make sure that it is functioning properly. If not needed, it is prefer not to leave a drain routinely unless there is a particular concern, e.g., bleeding. If needed, a drain may be left in situ through a separate stab wound incision. The wound is then closed in two layers. The dartos fascia is closed with 2-0 absorbable suture and the skin is closed with 3-0 absorbable suture.

EMBODIMENTS

A first embodiment provides a penile prosthesis, comprising a pump; a reservoir fluidically connected to the pump; at least one inflatable cylinder configured to inflate in response to actuation of the pump by a user to transfer fluid into the at least one inflatable cylinder; and at least one length-adjustable tube fluidically connecting the pump to the at least one inflatable cylinder and configured to adjust in length according to a patient's unique anatomy.

One aspect of the first embodiment provides the at least one length-adjustable tube includes an accordion-like structure configured to extend in length in response to an extension force longitudinally extending accordion-like structure.

One aspect of the first embodiment provides the accordion-like structure having two ends with one of the two ends attached to the pump and another of the two ends attached to the at least one inflatable cylinder, and the accordion-like structure is configured to extend in length by pulling the two ends away from each other.

One aspect of the first embodiment provides that the accordion-like is configured to reduce in length in by pushing the two ends of the accordion-like structure longitudinally toward each other.

One aspect of the first embodiment provides that the accordion-like structure is configured to decrease in length in response to a longitudinal contraction force contracting the accordion-like structure.

One aspect of the first embodiment provides that the at least one length-adjustable tube includes a nut configured to loosen and allows the at least one length-adjustable tube to be pulled from the pump to extend the length and pushed back into the pump to reduce the length.

One aspect of the first embodiment provides that the reservoir is fluidically connected to the pump through a second length-adjustable tube, wherein the second length-adjustable tube includes a second structural mechanism configured to adjust a length of the second length-adjustable tube according to a patient's unique anatomy.

One aspect of the first embodiment provides that the reservoir is fluidically connected to the pump through the second length-adjustable tube, a connector, and a flexible tube.

One aspect of the first embodiment provides that the connector connects the flexible tube to the length-adjustable tube.

One aspect of the first embodiment provides that the connector includes a male connector and a female connector, with the male connector being configured to connect with the female connector and wherein the male connector includes a plurality of protrusions disposed circumferentially about a tube and the female connector includes a plurality of openings, a tube and a circumferential recess disposed between the tube of the female connector and an outer shell of the female connector, the plurality of openings of the female connector being configured to receive the protrusions of the male connector.

One aspect of the first embodiment provides that the tube of the female connector is configure to insert into a lumen of the tube of the male connector.

One aspect of the first embodiment provides that the at least one inflatable cylinder includes a first inflatable cylinder and a second inflatable cylinder, and the at least one length-adjustable tube includes a first length-adjustable tube and a second length-adjustable tube.

One aspect of the first embodiment provides that the first length-adjustable tube and the second length-adjustable tube are configured to be individually adjusted according to the unique anatomy of the patient.

One aspect of the first embodiment provides a valve assembly arranged within the pump configured to actuate to release fluid in the at least one inflatable cylinder back into the reservoir to deflate at least one cylinder.

One aspect of the first embodiment provides that the at least one length-adjustable tube includes a nut configured to facilitate adjustment of the at least one length-adjustable tube and the nut is removably secured to the valve assembly.

A method embodiment provides a method of implanting a penile prosthesis, comprising inserting an inflatable cylinder into the penis; inserting a pump into the scrotum; connecting the pump and the inflatable cylinder with a length-adjustable tube; and adjusting a length of the length-adjustable tube according to a patient's unique anatomy.

One aspect of the method embodiment provides that the length-adjustable tube includes an accordion-like structure and adjusting the length the length-adjustable tube includes at least one of longitudinally extending the accordion-like structure or longitudinally contracting the accordion-like structure.

One aspect of the method embodiment provides that the length-adjustable tube includes a nut configured to loosen and allow adjusting of the length of the length-adjustable tube by pulling the length-adjustable tube from the pump to extend the length and pushing the length-adjustable tube back into the pump to reduce the length.

A second embodiment provides a penile prosthesis, comprising a pump; a valve assembly arranged with the pump; a reservoir fluidically connected to the pump by a first length-adjustable tube configured to adjust in length; and an inflatable cylinder fluidically connected to the pump by a second length-adjustable tube configured to adjust in length, the inflatable cylinder being configured to: inflate transfer fluid into the inflatable cylinder from the reservoir in response to actuation of the pump by a user, and deflate and release the fluid from the inflatable cylinder back into the reservoir in response to actuation of the valve assembly.

One aspect of the second embodiment provides that each of the first length-adjustable tube and the second-length adjustable tube are separable configured to adjust in length according to a patient's unique anatomy.

What is claimed is:

1. A penile prosthesis comprising:
an inflatable cylinder implantable into a penis;
a pump fluidically attachable to the inflatable cylinder through a first tube; and
a reservoir attachable to the pump through a second tube that is fluidically attachable between the pump and the reservoir, where the second tube comprises a first connector including a plurality of protrusions extending away from the first connector;
wherein the reservoir comprises a second connector comprising a conduit communicating with an interior of the reservoir and an outer shell spaced away from the conduit by a circumferential recess, with a plurality of openings formed in the outer shell of the second connector, and the plurality of openings are adapted to receive and mate with the plurality of protrusions of the first connector;
wherein the second tube is configured as a length-adjustable tube that fluidically connects the pump to the interior of the reservoir through the conduit, where the length-adjustable tube has a reduced-length mode and an extended-length mode configured to allow an adjustment of length in the second tube to adapt in response to a patient's unique anatomy and allow placement of the reservoir in an abdomen; and
wherein the pump further comprises an assembly that is sized to contain an excess length of the second tube, and the assembly comprises a nut coupling the length-adjustable tube to the pump, where the nut is configured to be loosened to allow the length-adjustable tube to be passed through the nut and away from the pump to provide the extended-length mode and to be passed through the nut and toward the pump to provide the reduced-length mode.

2. The penile prosthesis of claim 1, wherein the first connector is sized to fit into the circumferential recess of the second connector.

3. The penile prosthesis of claim 1, wherein the second tube comprises an accordion structure that is length-adjustable between the reduced-length mode and the extended-length mode.

4. The penile prosthesis of claim 1, wherein the first connector is a male connector and the second connector is a female connector, and the male connector is insertable into the female connector.

5. The penile prosthesis of claim 1, wherein the pump is fluidically attachable to the inflatable cylinder through the first tube, and the first tube is length-adjustable through a longitudinally extending accordion structure.

6. The penile prosthesis of claim 1, further comprising a valve assembly arranged within the pump and configured to release fluid from the inflatable cylinder back into the reservoir to deflate the inflatable cylinder.

7. The penile prosthesis of claim 1, wherein the second tube has a smooth surface.

* * * * *